Figure 1:
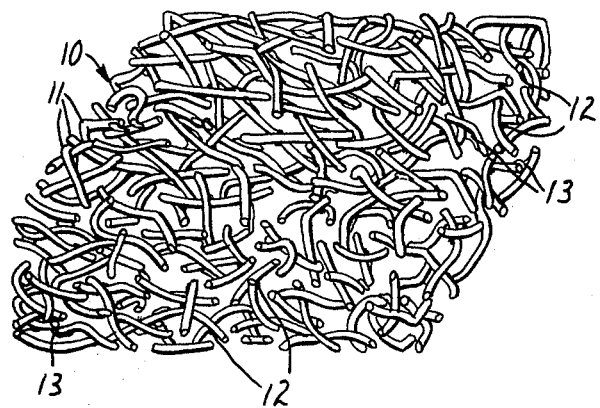

United States Patent [19]

Whitcomb

[11] 4,103,450
[45] Aug. 1, 1978

[54] INSECTICIDAL DEVICE

[75] Inventor: John F. Whitcomb, Mendota, Minn.

[73] Assignee: Minnesota Mining and Manufacturing Company, St. Paul, Minn.

[21] Appl. No.: 812,631

[22] Filed: Jul. 5, 1977

Related U.S. Application Data

[63] Continuation-in-part of Ser. No. 645,259, Dec. 29, 1975, abandoned.

[51] Int. Cl.² .............................................. A01M 1/20
[52] U.S. Cl. .................................... 43/131; 428/288; 428/289; 428/296
[58] Field of Search ...................... 428/288, 289, 296; 43/131

[56] References Cited

U.S. PATENT DOCUMENTS

| | | | |
|---|---|---|---|
| 3,295,246 | 1/1967 | Landsman et al. | 43/131 |
| 3,767,785 | 10/1973 | Bordenca | 43/131 |
| 3,837,988 | 9/1974 | Hennen et al. | 428/92 |
| 3,931,692 | 1/1976 | Hermanson | 43/131 |

Primary Examiner—James J. Bell
Attorney, Agent, or Firm—Cruzan Alexander; Donald M. Sell; Richard Francis

[57] ABSTRACT

A shaped device with insecticidal properties is provided by a lofty, open low-density web impregnated with an insecticidal substance. The web is formed of randomly disposed crimped or looped synthetic fibers bonded together at points where they touch and cross. The insecticidal substance may be selected from the group consisting of pyrethrum, endrin, aldrin and its epoxide, dieldrin, heptachlor, DDT, BHC and its isomer lindane, chlordane, methoxychlor, DDD or TDE, and toxaphene; organophosphate insecticides including malathion, parathion, TEPP, schradan, demeton, dimethoate, carbamates such as carbaryl and methyl carbamate, organic thiocyanates, haphthalene, and paradichlorobenzene; and chlorinated phenols, such as pentachlorophenol and tetrachlorophenol. The preferred insecticide is encapsulated pyrethrum.

5 Claims, 2 Drawing Figures

INSECTICIDAL DEVICE

RELATED APPLICATIONS

This application is a continuation-in-part of prior copending application Ser. No. 645,259 filed Dec. 29, 1975 now abandoned.

BACKGROUND OF THE INVENTION

The present invention relates to an insecticidal device provided by an insecticide-impregnated open low-density web.

For the housewife, nothing is more upsetting than to watch a parade of ants pass across a kitchen floor into the food storage cabinets. The infestation of insect pests has been a bane to mankind throughout history. Not only do ants present a problem, but other insects are equally repugnant because they are either bothersome, carry organisms which may produce disease, or both. The common housefly is perhaps one of the more frequently observed insect pests. Other common pests include gnats, mosquitoes, moths and cockroaches, but these are just a few of a multitude.

From the very beginning, man has sought means for eradicating insect pests or isolating himself from their presence. Early attempts involved placing sticky substances at locations where the insects would be required to pass. These attempts may have led to the development of the product which we have come to know as "fly paper", which is merely a strip of material covered with a sticky substance. Such a product is described in U.S. Pat. No. 813,196 issued in 1906 to Julius H. Bien. Another means of eradicating insects involved trapping them in insect traps which may include a housing containing an insect attractant and a tacky substance. Such traps have become more and more sophisticated and complex; see U.S. Pat. No. 3,755,958 for a typical example.

Perhaps the most common present-day means of eradication of insects is by application of insecticides, either by vaporization of this material or by its application to a suitable carrier strip or device. Vaporization has its disadvantages in that there is very little control over the dispersal of the insecticide and it may spread into areas where it is not wanted. Vaporization may be accomplished by use of a conventional aerosol dispenser or by means of a plastic strip which exudes insecticide vapors, a popular form of the latter being sold under the trade designation "Shell No Pest Strip" by the Shell Chemical Company. Application of the insecticide to a carrier strip such as a sheet of paper or tape may alleviate the dispersal problem, but it reduces considerably effective quantities of available insecticice.

SUMMARY OF THE PRESENT INVENTION

The present invention provides a novel insecticide-bearing article which provides a highly expanded surface bearing the insecticide yet which permits control over the dispersal of this material. The insecticidal device of the invention is provided by insecticide-impregnated lofty, open low-density web. The insecticide may be pyrethrum, endrin, aldrin and its epoxide, dieldrin, heptachlor, DDT, BHC, and its isomer lindane, chlordane, methoxychlor, DDD or TDE, and toxaphene; organophosphate insecticides including malathion, parathion, TEPP, schradan, demeton, dimethoate, carbamates such as carbaryl and methyl carbamate, organic thiocyanates, haphthalene, and paradichlorobenzene; and chlorinated phenols, such as pentachlorophenol and tetrachlorophenol. The web is formed of randomly disposed crimped or looped synthetic fibers bonded together at points where they touch and cross. The low-density web provides the expanded surface upon which the insecticide may be deposited. The web has an open porous lofty structure which will permit passage of the smaller-size insects such as ants, mites, lice and the like.

Segments of the insecticide-impregnated web of the invention may be placed at various locations in the area being treated to permit exposure to insects. Thereafter, the insecticide-bearing web may be removed, leaving little, if any, insecticide residue in the treated area. The web segments are compressible yet they will spring back to their original shape, thus, they can be forced into small spaces such as behind kitchen appliances and in other crevices where insects may be expected to be found. When so installed, the device of the invention will not block the path of the insect, but will create a lethal zone for the insect to pass through and be exposed to the insecticide. The web may also contain an insect attractant to entice the insect into the web. After the insect problem has been successfully resolved, the device may be removed and discarded.

DRAWING

Figure 2:
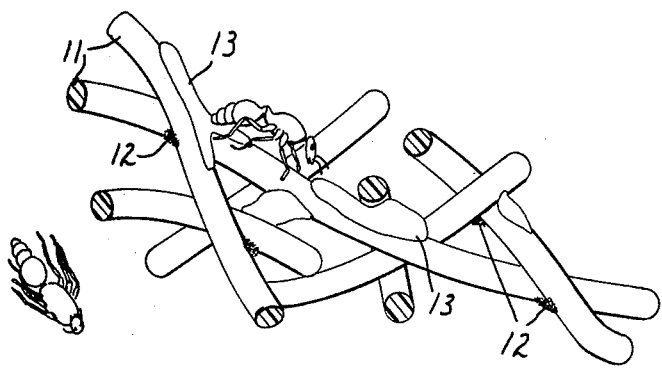

For convenience in visualizing the article of this invention, attention is directed to the accompanying drawing in which:

FIG. 1 represents a view in perspective of an insecticide-impregnated open low-density non-woven pad formed of bonded randomly disposed crimped or looped synthetic fibers; and FIG. 2 represents a greatly enlarged segmental view of a plurality of fibers as may be typically encountered in the web shown in FIG. 1.

As shown in FIG. 1 and in greater detail in FIG. 2, an insecticide-impregnated web 10 is formed of randomly disposed and interlaced crimped or looped synthetic fibers 11 which have been coated with insecticide and which are bonded together at points where they cross and contact each other. Such bonding may be by application of adhesive resin 12 at the locations where fibers 11 contact one another or without the use of adhesive resin by forming the web by a process which autogeneously bonds the fibers together. Processes which produce autogeneously bonded webs are disclosed in assignee's U.S. Pat. Nos. 3,837,988 or 3,686,049.

Insecticide 12 coats the fiber surfaces of the web. Some insecticides will readily adhere to the surface of synthetic fibers. Other insecticides may require a first application of a tacky substance to the fiber surface, especially for dry powdery insecticides. Other insecticides may require that they be blended with a compatible binder to form a mixture which will adhere to the web.

The non-woven webs upon which the insecticide will be coated to produce the insecticidal device of the invention are generally characterized by their extreme openness, low-density, and loftiness. These webs typically have a void volume within the range of about 85 to 97 percent. The webs may be formed of any filament-forming synthetic polymeric material such as polyester (preferably polyethylene terephthalate), nylon, polyvinyl chloride, polyacrylate and the like. Typical fiber sizes which have been found to be useful will be on the order of 6 to 200 denier, preferably on the order of 15 to 50 denier. The web should be at least 0.5 cm thick. Typical web thicknesses will vary between 0.5 and 5.0 cm. The web may be any convenient shape or size. Flat discs and rectangular shapes are typical, but any of a wide variety of other shapes may be used. Typical useful sizes may vary from 1 inch in diameter or width to 10 inches or more.

The adhesively bonded webs are generally formed of crimped, staple fibers by well-known techniques. Such fibers may be formed into a web by utilizing a "Rando-Webber" or "Rando-Feeder" machine sold by the Curlator Corporation, Rochester, New York, and described in U.S. Pat. Nos. 2,744,294, 2,700,188, 2,451,915 and 2,703,441.

The web fibers may be bonded together with any one of a variety of well-known adhesive binder materials. The adhesive binder may be either a thermosetting binder or a thermoplastic binder. The binder, of course, should be selected to be compatible with the particular substance forming the fibers and with the particular insecticide material being utilized. Binders which have been found to be particularly suitable for use in bonding the fibers together to produce a non-woven web include phenol-aldehyde resins, butylated urea aldehyde resins, epoxide resins, polyurethane resins, and polyester resins. The amount of binder employed to adhere the fibers together will be the minimum consistent with bonding the fibers together at their points of contact to provide an integral self-supporting web. Too little binder may produce a structure which sheds filaments containing insecticide and may create a residue problem. Too much binder would, of course, be uneconomical. Vastly too much binder may clog the web and reduce its porous and open nature.

Quite surprisingly, a suitable adhesively bonded non-woven mat is provided by the non-woven abrasive product sold under the trade designation "SCOTCH-BRITE" by the 3M Company of St. Paul, Minnesota. The method of preparing this product is described in the Hoover et al patent (U.S. Pat. No. 2,958,593), the disclosure of which is incorporated herein by reference.

The autogeneously bonded non-woven webs may be prepared by the process described in assignee's U.S. Pat. Nos. 3,837,988 and 3,686,049, as previously mentioned. Briefly, as disclosed in these patents, autogeneously bonded webs may be prepared by extruding a filament-forming thermoplastic material in the form of a bundle of filaments which is directed toward a contact surface and quench bath where filaments are permitted to coil, entangle and adhere to one another as they cool and solidify to produce a lofty, porous integral web. A commercially available form of this material is sold by the 3M Company under the trade designation "NO-MAD" surfacing material. The disclosures of U.S. Pat. Nos. 3,837,988 and 3,686,049 are incorporated herein by reference for their teachings of the method of preparing autogeneously bonded webs.

The insecticide may be selected from any of a variety of materials known to be toxic to insects. Since a particular insecticide is generally not lethal to all insects, the insecticide should, of course, be selected for the particular insect desired to be eradicated. Commonly used insecticides include those which are derived from plants such as pyrethrum which is derived from the flower of one species of the chrysanthemum; synthetically prepared contact insecticides such as chlorinated hydrocarbons including endrin, aldrin and its epoxide, dieldrin (all chlorinated naphthalenes), heptachlor, DDT, BHC and its isomer lindane, chlordane, methoxychlor, DDD or TDE, and toxaphene; organophosphate insecticides including malathion, parathion, TEPP, schradan, demeton, dimethoate, carbamates such as carbaryl and methyl carbamate, organic thiocyanates such as "Thanite", "Lethane 384" "Lethane 60", naphthalene, and paradichlorobenzene; and chlorinated phenols, such as pentachlorophenol and tetrachlorophenol. Compounds known as polychlorinated biphenyls (PCBS) may be added to formulas containing chlorinated hydrocarbon insecticides to increase their toxicity and persistence.

The preferred insecticide composition is a microencapsulated pyrethrum disclosed in assignee's U.S. Patent application Ser. No. 566,287, filed Apr. 9, 1975, now abandoned in favor of copending U.S. Patent application Ser. No. 717,170, filed Aug. 24, 1976. The disclosure of the last-mentioned patent application is incorporated herein by reference as to the teaching of the preparation of the microencapsulated pyrethrum. Pyrethrum is encapsulated because it is unstable in the presence of ultraviolet light and atmospheric oxygen. Encapsulation increases its useful life.

The amount of insecticide utilized is relatively unimportant but it should not be so much as to clog the web and thus reduce its open and porous nature. The amount will, of course, depend upon the volatility of the insecticide. Sufficient quantities of highly volatile insecticide should be utilized to assure a toxic level for a sufficient time to completely eradicate the problem insects. Typical weights of insecticide for a 10-millimeter thick web may vary between 1–20 milligrams per square centimeter of web.

While the insecticidal device described herein has been indicated as being primarily useful for eradication of insects of the size which may pass through the web, it is also useful for insects of a larger size and for insects which would not have a propensity to pass through the web, e.g., such as a common housefly. The high void volume of the web provides a high concentration of insecticide within a close proximity of the web for some insecticides, providing a lethal zone adjacent the web which is highly effective in killing insects which may come within this zone. The web may also be hung in an elevated place to permit vaporization and dispersal of the insecticide so that it may be effective against flying insects as well. It has been found to be extremely effective when hung in the attic of a home.

The insecticide device of the invention may also include an attractant substance within the web to entice the insects therein. The attractant substance may be in the form of food or may be a sex (or mating) attractant, a swarming attractant or the like. Known sex attractants include riblure, propylure, hexylure and grandlure. The attractants may be effective by themselves, may require a synergist, or may be used in combinations. The type of attractant used will depend entirely upon the type of insects desired to be trapped, and would be obvious to those skilled in the art. Generally, such substances are naturally occurring and substantially non-toxic.

The invention is further illustrated by the following non-limiting examples, wherein all parts are by weight unless otherwise indicated.

EXAMPLE 1

An insecticidal device according to the invention was prepared by coating a 4 inch by 5 inch by ⅜ inch non-woven web of crimped bonded synthetic fibers with an encapsulated pyrethrum insecticide to provide a dry insecticide coating weight of 0.06 g per sq. cm. The non-woven web was an abrasive product sold under the trade designation "SCOTCH-BRITE" scouring pad No. 96 by the 3M Company of St. Paul, Minnesota. This abrasive product was formed of 15 denier, 40 millimeter, crimped nylon fibers which have been impregnated with a phenol-aldehyde adhesive which contained aluminum oxide filler abrasive particles, according to the disclosure of the aforementioned U.S. Pat. No. 2,958,593. The encapsulated pyrethrum was applied from an aerosol container pressurized with hydrocarbon repellent as a mixture of 3.6 parts sodium lauryl sulfate, 6 parts encapsulated pyrethrum (prepared according to the disclosure of the aforementioned U.S. application Ser. No. 566,287), and water.

EXAMPLE 2

An insecticidal device was prepared by coating the non-woven web described in Example 1 with a non-encapsulated pyrethrum insecticide composition to provide a dry insecticide coating weight of 0.007 g per sq. cm. The pyrethrum insecticide was that available under the trade designation "d-con Warpath" from the d-con Company.

EXAMPLE 3

An insecticidal device was prepared by coating the non-woven web described in Example 1 with a non-encapsulated pyrethrum insecticidal composition sold under the trade designation "Dracket Insect Killer" by the Dracket Product Company to produce a dry coating weight of 0.003 grams per sq. cm.

EXAMPLES 4–9

Examples 4–9 were prepared by coating a 3½ inch × 5 inch × 1 inch non-woven web of crimped bonded synthetic polyester fibers with the insecticide compositions described in Table 1 below.

TABLE 1

| Ex. No. | Insecticide | Insecticide Wt. (g) |
|---|---|---|
| 4 | Encapsulated Pyrethrum | 0.0399 |
| 5 | Encapsulated Pyrethrum | 0.0223 |
| 6 | Encapsulated Pyrethrum | 0.0215 |
| 7 | Encapsulated Pyrethrum | 0.0315 |
| 8 | "Pyrosol booster" | 0.2302 |
| 9 | "Buggy Whip" | 0.131 |

The non-woven web was an abrasive product sold under the trade designation "SCOTCH-BRITE" "Pot 'n Pan Handler" by the 3M Company of St. Paul, Minnesota. This abrasive product was formed of crimped 200 denier polyester filaments bonded together with a phenol aldehyde binder material which contained aluminum oxide abrasive particles, according to the disclosure of the aforementioned U.S. Pat. No. 2,958,593. The webs weighed about 11–12 grams prior to coating.

The encapsulated pyrethrum insecticide was substantially as described in Example 1. One part of a mixture of 1.2 parts pyrethrum and 6.03 parts piperonyl butoxide diluted with 4 parts water provided the insecticide coating mixture for Examples 10–11. Examples 12 and 13 were coated with one part of a mixture of 1.25 parts pyrethrum and 6.62 parts piperonyl butoxide, which mixture was diluted with 4 parts water.

"Pyrosol booster" is the trade designation of an insecticide composition sold by the Lynde Chemical Company of Minneapolis, Minnesota, containing 73.7% petroleum distillates, 13% piperonyl butoxide, 1.3% pyrethrum, and 12% inert ingredients. One part of the "Pyrosol booster" was diluted with 4 parts water for application. "Buggy Whip" is the trade designation of an insecticide composition sold by the S. C. Johnson and Son Company of Racine, Wisconsin, containing 0.4% pyrethrum, 2.0% piperonyl butoxide, 1.6% petroleum distillate, and 96% inert ingredients. "Diazinon 4E" is the trade designation of a Ciba-Geigy Company insecticide composition prepared according to the disclosure of U.S. Pat. No. 2,754,243, and containing 47.5% diazinon, 26.2% petroleum distillate, and 26.3% inert ingredients. One part "Diazinon 4E" was diluted with 9 parts water for application.

EXAMPLES 10–17

Examples 10–17 were prepared utilizing a 4 inch × 5 inch × ⅜ inch non-woven web of crimped bonded synthetic fibers with the insecticide compositions shown in Table 2 to produce insecticidal devices containing the dry insecticide weights indicated in Table 2 below.

TABLE 2

| Ex. No. | Insecticide | Insecticide Wt. (g) |
|---|---|---|
| 10 | Encapsulated Pyrethrum | 0.0501 |
| 11 | Encapsulated Pyrethrum | 0.0556 |
| 12 | Encapsulated Pyrethrum | 0.0450 |
| 13 | Encapsulated Pyrethrum | 0.0601 |
| 14 | "Pyrosol booster" | 0.2791 |
| 15 | "Buggy Whip" | 0.2798 |
| 16 | "Diazinon 4E" | 0.1859 |
| 17 | "Diazinon 4E" | 0.1912 |

The non-woven web weighed approximately 7–8 grams before coating. The non-woven web is the abrasive product described in Example 1. The insecticide compositions are described in the descriptions following Table 1.

BIOLOGICAL ACTIVITY EVALUATION

Certain of the Examples were evaluated for biological activity by placing a test sample according to the invention in a 12 inch × 15 inch × 5 inch high box containing 20 cockroaches. Each of the test samples had been allowed to dry for at least a 6-hour period before testing. The sides of the box were greased and talc-coated so that the cockroaches would be unable to escape. A beer-soaked dog food pellet was placed on top and in the center of each test pad to attract the cockroaches. The cockroach mortality was recorded after 24, 48 and 96 hours, respectively. Results are shown in Table 3 below.

TABLE 3

| Ex. No. | 24 Hour % Kill | 48 Hour % Kill | 96 Hour % Kill |
|---|---|---|---|
| 4 | 0 | 0 | 40 |
| 7 | 0 | 0 | 10 |
| 8 | 0 | 0 | 25 |
| 9 | 20 | 20 | 20 |
| 10 | 0 | 100 | — |
| 11 | 0 | 100 | — |
| 12 | 0 | 10 | — |
| 13 | 0 | 80 | — |
| 14 | 0 | 100 | — |
| 16 | 100 | — | — |
| 17 | 0 | 100 | — |

Certain of the Examples were further evaluated for biological activity by utilizing a forced exposure evaluation procedure which involved placing a test sample into an open glass cylinder and placing five cockroaches upon the test sample. The size of the bottom of the cylinder was such that the cockroaches were required to remain on the surface of the test pad. The group of five cockroaches were exposed for 30 minutes and removed. These roaches were observed subsequently and the number dying within 30 minutes observed. The number dying in the following 24 hours and 48 hours was also observed. After a period of 5 days, a new set of five cockroaches was placed on the test pad and again left there for 30 minutes. These were also removed and the number dying after 30 minutes, 24 hours and 48 hours observed. The same procedure was repeated after 7 days. Table 4 below sets forth the percentage of cockroaches killed after each of these exposure times.

TABLE 4

| Ex. No. | Time (hr.) | 1st day | 5th day | 7th day |
|---|---|---|---|---|
| 10 | ½ | 0 | 0 | 0 |
|  | 24 | 20 | 60 | 80 |
|  | 48 | 20 | 100 | 80 |
| 11 | ½ | 0 | 40 | 40 |
|  | 24 | 0 | 40 | 60 |
|  | 48 | 0 | 60 | — |
| 12 | ½ | 20 | — | 60 |
|  | 24 | 40 | 80 | 100 |
|  | 48 | 40 | 80 | — |
| 13 | ½ | 60 | — | 100 |
|  | 24 | 80 | 80 | 100 |
|  | 48 | 80 | 80 | — |
| 14 | ½ | 100 | 80 | 100 |
|  | 24 | 100 | 100 | 80 |
|  | 48 | 100 | 100 | — |
| 15 | ½ | 100 | 100 | 100 |
|  | 24 | 100 | 100 | 100 |
|  | 48 | 100 | 100 | — |
| 16 | ½ | 100 | 50 | 80 |
|  | 24 | 100 | 100 | 80 |
|  | 48 | 100 | 100 | — |
| 17 | ½ | 100 | 100 | 80 |
|  | 24 | 100 | 100 | 100 |
|  | 48 | 100 | 100 | — |

TABLE 4-continued

| Ex. No. | Time (hr.) | 1st day | 5th day | 7th day |
|---|---|---|---|---|

What is claimed is:

1. An insecticidal device which can be deposited in areas infested with undesirable insects and after use easily removed, comprising an insecticidal substance impregnating and coating the fiber surfaces of a lofty, low-density, open non-woven web which will permit the passage therethrough of smaller-size insects such as ants, mites and lice, and has a thickness of at least 0.5 cm thick and a void volume within the range of about 85 to 97 percent, said web being formed of randomly disposed crimped or looped synthetic fibers having a fiber size on the order of 6 to 200 denier and being bonded together at points where they touch and cross, said insecticidal substance being selected from the group consisting of pyrethrum, endrin, aldrin and its epoxide, dieldrin, heptachlor, DDT, BHC, lindane, chlordane, methoxychlor, DDD, TDE, toxaphene, malathion, parathion, TEPP, schradan, demeton, dimethoate, carbaryl and methyl carbamate, organic thiocyanates, haphthalene, paradichlorobenzene, pentachlorophenol, and tetrachlorophenol.

2. The insecticidal device of claim 1 wherein said web is formed of staple fibers which have been bonded together at the points where they touch and cross by an adhesive composition.

3. The insecticidal device of claim 1 wherein the insecticide is encapsulated pyrethrum.

4. The insecticidal device of claim 1 wherein said web is in the order of 0.5 to 5 cm thick.

5. The insecticidal device of claim 1 wherein said fibers are autogeneously bonded together.

* * * * *